United States Patent [19]
Bruijns

[11] Patent Number: 5,778,044
[45] Date of Patent: Jul. 7, 1998

[54] X-RAY EXAMINATION APPARATUS INCLUDING AN IMAGE PICK-UP APPARATUS WITH A CORRECTION UNIT

[75] Inventor: Antonius J. C. Bruijns, Eindhoven, Netherlands

[73] Assignee: U.S. Philips Corporation, New York, N.Y.

[21] Appl. No.: 773,118

[22] Filed: Dec. 26, 1996

[30] Foreign Application Priority Data

Dec. 27, 1995 [EP] European Pat. Off. ............ 95203645

[51] Int. Cl.$^6$ ........................................... H04N 1/00
[52] U.S. Cl. .................. 378/98.7; 378/92.8; 378/98.12
[58] Field of Search ...................... 378/98.2, 98, 98.3, 378/98.7, 98.8, 98.12, 98.11

[56] References Cited

U.S. PATENT DOCUMENTS 5,452,338  9/1995  Granfors et al. ............. 378/98.11
5,602,896  2/1997  Diepstraten ..................... 378/98.7

FOREIGN PATENT DOCUMENTS

0562657A2  9/1993  European Pat. Off. ....... H04N 5/217

*Primary Examiner*—David P. Porta
*Attorney, Agent, or Firm*—Jack D. Slobod

[57] ABSTRACT

An X-ray examination apparatus includes an X-ray image intensifier for deriving an optical image from an X-ray image. The optical image is picked up by means of an image pick-up apparatus which includes a correction unit which is arranged to form a dark image signal and to derive test image signals from the optical image. Correction values are derived on the basis of the test image signals and the dark image signal. The correction unit is arranged to form a dark image signal, to derive one or more test image signals from the optical image, and to derive the correction values from said test image signals and the dark image signal. The dark image signal is picked up in the absence of incident light on the image sensor. The test image signals have a signal level which represents brightness values of the optical image which have been amplified by individual gain values.

14 Claims, 3 Drawing Sheets

X-RAY EXAMINATION APPARATUS INCLUDING AN IMAGE PICK-UP APPARATUS WITH A CORRECTION UNIT

BACKGROUND OF THE INVENTION

1. Field of the Invention

The invention relates to an X-ray examination apparatus, including an X-ray detector for deriving an optical image from an X-ray image, an image pick-up apparatus for deriving an image signal from the optical image, and a correction unit for correcting the image signal by means of correction values. The invention also relates to an X-ray examination apparatus of this kind which includes an image pick-up apparatus provided with one or more image sensors for deriving electronic sub-image signals from sub-images of an optical image, a combination unit for combining, on the basis of the electronic sub-image signals, an electronic image signal for a composite image, and a correction unit for deriving corrected brightness values of the sub-images from correction values and the electronic sub-image signals. The invention also relates to methods of correcting an electronic image signal, in which the electronic image signal is derived from an optical image by means of an image sensor and corrected brightness values are derived from the electronic image signals and correction values, or in which sub-image signals are derived from sub-images of the optical image by means of one or more image sensors and corrected brightness values are derived from the electronic sub-image signals and correction values.

2. Description of the Related Art

An X-ray examination apparatus, an image pick-up apparatus and a method of this kind are known from European Patent Application EP 0 562 657.

SUMMARY OF THE INVENTION

The known X-ray apparatus includes an X-ray source and an X-ray image intensifier whereto the image pick-up apparatus is optically coupled. The X-ray source emits an X-ray beam for irradiating an object, for example a patient to be examined, so as to form an X-ray image. The X-ray image is formed on an entrance screen of the X-ray image intensifier and converted into an optical image on an exit window of the X-ray image intensifier. The optical image is picked up and converted into an electronic image signal by the image pick-up apparatus. The correction unit of the image pick-up apparatus in the known X-ray examination apparatus is arranged to form the corrected brightness values by multiplying, for individual pixels in the optical image, signal levels of the electronic image signal by the reciprocal value of an attenuation coefficient associated with the relevant pixel. The reciprocal values act as correction values. In the known X-ray apparatus the attenuation coefficients are obtained by forming an image of a homogeneous object and by deriving the attenuation coefficient for individual pixels as the ratio of the brightness value of the relevant pixel in the image of the homogeneous object to the maximum brightness value in said image. In the known X-ray examination apparatus the fact that signal levels representing the brightness values contain a DC component is not taken into account for the extraction of the correction values. When the variation of the correction values is small in comparison with said DC component, the correction values cannot be accurately determined. Moreover, in the DC component a variation occurs which is caused inter alia by the dark current contributions of the image sensors used, for example due to temperature fluctuations. Because the correction values supplied by the correction unit of the known X-ray examination apparatus contain inaccuracies, disturbances still occur, degrading the diagnostic quality of an image composed by means of the corrected brightness values derived on the basis of said correction values. Because of such disturbances, notably small details of low contrast, such as an image of a small tumor or another anomaly in the anatomy of a patient to be examined, cannot be suitably distinguished in the image. Undesirable differences between signal levels of individual image sensors have been found to be dependent on settings of the X-ray examination apparatus or of the image pick-up apparatus and if only a single set of correction values were available, an electronic image signal representing an image of high diagnostic quality could not be formed for individual settings.

In a further embodiment of the known X-ray examination apparatus, light emanating from the exit screen is split, via a beam splitter including a partly transparent mirror, into two sub-images which are picked up by individual image sensors.

This embodiment of the known image pick-up apparatus includes two solid-state image sensors, each of which comprises a plurality of photosensitive elements. The image sensors are arranged in such a manner that image elements of the optical image which are picked up by the photosensitive elements of one image sensor are mapped in the intermediate spaces between the photosensitive elements of the other image sensor. Each of the image sensors picks up a sub-image and applies an electronic sub-image signal to the combination unit which forms an electronic sub-image signal for the composite image from the electronic sub-image signals. For example, the composite image is composed in such a manner that odd image lines have been picked up by one sensor and even image lines by the other sensor. An alternative method of forming a composite image is to select alternately image elements picked up by means of the individual image sensors as pixels of the composite image. The composite image has a spatial resolution which is higher than that of the individual sub-images.

In order to counteract disturbances in the composite image due to signal levels of individual sub-image signals being different, even though said signal levels relate to substantially the same image information in the optical image, the known image pick-up apparatus comprises a correction unit. The correction unit multiplies signal levels of the sub-image signals representing brightness values of the sub-images by correction values in order to form corrected brightness values of the composite image. The composite image has a high diagnostic quality because small details, even those of low contrast, can be reproduced therein in a suitably visible manner. The correction unit compensates differences between sensitivities of the individual image sensors and differences between vignetting in the individual sub-images. The known image pick-up apparatus utilizes predetermined correction values which are stored, for example in a memory. The correction values will be inaccurate notably when the signal levels of the sub-image signals have a comparatively large DC component. Undesirable differences between signal levels of individual image sensors have been found to be dependent on settings of the X-ray examination apparatus or of the image pick-up apparatus, so that it would not be possible to form a composite image of high diagnostic quality for individual settings if only a single set of correction values were available. The known X-ray apparatus has separate sets of correction values available for individual settings. For example, separate sets of correction values which have been selected on the basis of a diaphragm setting of the image pick-up apparatus are stored in a memory. In the known X-ray examination apparatus, however, undesirable differences between signal levels of the electronic sub-image signals cannot always be avoided so as to counteract disturbances in the composite image, because the number of sets of correction values that can be stored may be large but must nevertheless remain limited. Consequently, circumstances may arise in which the known correction unit does not adequately succeed in deriving suitably corrected brightness values so as to form the composite image without disturbances.

It is an object of the invention to provide an X-ray examination apparatus which includes an image pick-up apparatus with a correction unit whereby correction values can be obtained which are more accurate than those that can be obtained by means of the known X-ray examination apparatus. It is a further object of the invention to provide an X-ray examination apparatus which includes an image pick-up apparatus enabling compensation of undesirable differences between signal levels of individual sub-image signals to be maintained while the circumstances in which images are generated change.

This object is achieved by means of an X-ray examination apparatus according to the invention which is characterized in that the image pick up apparatus is arranged to form a dark image signal ($I_1$, $I_2$, $I_3$) and that the correction unit is arranged to derive one or more test image signals ($I_4$, $I_5$, $I_6$) from the optical image, and to derive the correction values from said test image signals and the dark image signal.

The dark image signal is picked up in the absence of light incident on the image sensor. The signal level of the dark image signal represents inter alia thermal noise in the image sensor. The signal levels of the test image signals represent brightness values of the optical image for individual amplifications. For deriving the correction values, the dark image signal is used to compensate that a shift of the signal level of the test image signals. This shift is the DC component, or "offset", of the test image signals and is independent of the brightness of the optical image. By taking this offset into account in determining the correction values, more accurate results are obtained for the correction values, notably if the offset is large relative to the differences between correction values for individual positions in the optical image. Moreover, as a result of the use of the dark image signal for deriving the correction values, fluctuations in the offset are compensated. These fluctuations are caused, for example by temperature fluctuations which cause variations in the dark current contribution of the image sensor. As the dark image signal is formed as much as possible in the same circumstances (except for the exposure of the image sensor) as those in which the electronic image signal is derived, such fluctuations can be compensated better. The dark image signal is preferably formed immediately before or immediately after the extraction of the electronic image signal. The corrected brightness values are used, for example as signal levels of a corrected electronic image signal. Using the corrected electronic image signal, the image formed by the corrected brightness values can be displayed, for example by applying the corrected electronic image signal to a monitor.

Because the correction values are derived on the basis of brightness values of the optical image, it is achieved that the corrected brightness values have substantially the same value in as far as they relate to substantially the same brightness values in the optical image or the X-ray image. When the optical image changes, if necessary the correction values are adapted in order to derive corrected brightness values on the basis of the changed brightness values of the optical image, which corrected brightness values again have substantially the same value, in the changed conditions, in as far as they relate to substantially the same image information. The optical image may change, for example because the setting of the X-ray source or of a diaphragm of the image pick-up apparatus is changed, or because the image information changes due to motions of the patient, for example due to respiration or pulsation of the heart.

A preferred embodiment of an X-ray examination apparatus according to the invention is characterized in that the correction unit is arranged to derive an offset correction value from one or more of the test image signals and the dark image signal, which offset correction value represents a difference between the minimum signal level of the electronic image signal and a zero level.

For the zero level a predetermined reference level or, for example the mean signal level or the minimum signal level of the dark image signal can be chosen. The offset correction values compensate an offset of the signal level of the electronic image signal in the corrected brightness values. The brightness of an image composed by means of said corrected brightness values is not disturbed by offset of the signal level of the electronic image signal or by fluctuations of the offset.

Use can also be made of an image pick-up apparatus which includes one or more image sensors for deriving electronic sub-image signals from sub-images of the optical image. This image pick-up apparatus composes an electronic image signal for a composite image on the basis of said sub-image signals. For the zero level the minimum signal level of one of the electronic sub-image signals can then be chosen. The offset correction value is used to compensate a difference between signal levels of the electronic sub-image signals in as far as they relate to substantially the same image information and are independent of the brightness of the optical image. Such a difference, being independent of the brightness of the optical image, is referred to as an offset difference. The offset difference is compensated by the offset correction value derived from a test image signal and the dark image signal, even if said difference varies, for example as a function of a setting of the X-ray examination apparatus. An offset difference is, generally speaking, dependent on the temperature of the image sensors. This is because a major cause of offset difference consists in a difference between temperature-dependent dark currents of individual image sensors.

A further preferred embodiment of an X-ray examination apparatus according to the invention is characterized in that the correction unit is arranged to derive a gain correction value from the test image signals and the dark image signal, which gain correction value represents a ratio of a signal level of the electronic image signal to a reference value.

The reference value is, for example the mean brightness value of a predetermined part (usually the central part) of the optical image; in that case preferably an image of a uniform test object is used to derive the correction values. Because the gain correction value is determined by means of the dark image signal, more accurate results are obtained for the correction values in comparison with the known X-ray examination apparatus. The results are more accurate notably when the variation of the gain correction values is small with respect to the offset of the electronic image signal. Said accurate correction values enable corrected brightness values to be obtained in which disturbances have been substantially counteracted. Counteracted are notably variations in the correct brightness values which do not relate to image information in the optical image or the X-ray image. A cause of such variations consists in that variations which do not relate to image information may appear in the electronic image signal due to vignetting by an optical system which images the optical image on the image sensor or due to imaging faults arising in an X-ray image intensifier deriving the optical image from the X-ray image.

Vignetting may be introduced by an optical system which couples the image pick-up apparatus to the exit window of the X-ray image intensifier. Artefacts in the optical image may also arise because the electron-optical image used in the X-ray image intensifier exhibits more or less deviations from the ideal image. Such deviations cause brightness variations in the optical image which do not relate to image information in the X-ray image. The corrected brightness values of the composite image enable the image information of the X-ray image to be reproduced with a high diagnostic quality. This means that small details of low contrast can still be reproduced in a clearly visible manner, for example on a monitor or as a hard copy.

The gain correction values correct brightness values of the sub-images for differences between signal levels of the sub-image signals which relate to substantially the same image information and in as far as these differences are dependent on the brightness of the optical image. Such differences are referred to as gain differences and are caused inter alia by differences between the sensitivities of individual image sensors. Vignetting caused by an optical system whereby the optical image is imaged on the image sensor (sensors) may also be a cause of gain differences.

When use is made of an image pick-up apparatus with two or more image sensors, brightness values of a sub-image of one of the image sensors can be used as a reference value. The brightness values of positions in this reference image are then used as reference values for the positions in the sub-images picked up by means of another image sensor. It is ensured that positions in the reference image correspond to positions in the relevant sub-image, i.e. that corresponding positions relate to substantially the same image information, for example because they relate to substantially the same position in the optical image.

A further preferred embodiment of an X-ray examination apparatus according to the invention is characterized in that the correction unit is arranged to form a first test image signal ($I_1$), having a signal level which corresponds to a brightness value of the optical image, a second test image signal ($I_7$), having a signal level which corresponds to the sum of an offset and a brightness value of the optical image which has been amplified by a first gain value ($G_0$) and a first difference signal ($I_4'$) which corresponds to the difference between signal levels of the first test image signal and the dark image signal, and that the correction unit includes an arithmetic unit which is arranged to derive the first gain value from signal levels of the second test image signal ($I_7$) and of the first difference signal ($I_4'$), and to derive the offset correction value ($\alpha$) from the first gain value and the signal levels of the second test image signal and of the first difference signal.

Using such a correction unit, an accurate result is obtained for the offset correction value. Because the second test image signal, containing an offset, is used to determine the offset correction value, the effect of unintended shifts of the signal level on the offset correction value is counteracted. Moreover, the first gain value can be suitably chosen without it being necessary to measure or pick up said first gain value separately. Because the first gain value is derived from the second test image signal and the first difference signal, it is not necessary either to take up any changes in the first gain value.

A further preferred embodiment of an X-ray examination apparatus according to the invention is characterized in that the arithmetic unit is arranged to derive the first gain value ($G_0$) from statistical variations of the signal levels of the second test image signal and of the first difference signal, and to derive the offset correction value a from the first gain value and mean values of the signal levels of the first difference signal and the second test image signal.

Statistical variations are to be understood to mean, for example mean values, maximum values or median values. Deriving the first gain value from such statistical variations, counteracts the disturbing of the value of said first gain values by unintended variations of signal levels such as noise. Moreover, the effect of such unintended variations of signal levels on the value of the offset correction value is also counteracted, because such mean values of said signal levels are insensitive to noise.

A further preferred embodiment of an X-ray examination apparatus according to the invention is characterized in that the correction unit is arranged to derive an offset-corrected electronic image signal from the electronic image signal and the offset correction value, to derive relative gain values for individual image elements in the optical image from signal levels of the offset-corrected electronic image signal and a reference value, to form a third ($I_5$) and a fourth ($I_6$) test image signal, having signal levels corresponding to brightness values of the optical image amplified by a second ($G_1$) and a third ($G_2$) gain value, respectively, and to form second ($I_5'$) and third ($I_6'$) difference signals which correspond to the difference between signal levels of second and third test image signals and the dark image signal, respectively, and that the arithmetic unit is arranged to derive an approximated gain value ($\beta$) from signal levels of the second and third difference signals, which approximated gain value represents an estimate for the relative gain values.

A reasonably accurate approximation for a gain correction value is derived from the approximated gain value and said reference values. This gain correction value compensates variations in the signal levels of the electronic image signal in as far as these variations do not relate to image information in the X-ray image or the optical image, but are dependent on the brightness of the optical image. When offset differences as well as gain differences are corrected, the corrected brightness values yield an image of high diagnostic quality. Notably small details of low contrast can be reproduced in a suitably visible manner, because brightness variations which do not relate to image information in the X-ray image or in the optical image are counteracted. Notably disturbances of brightness values due to offset in the electronic image signal as well as those due to vignetting are counteracted.

Not only the correction values can be adapted to changing circumstances in which images are picked up, but the results for the correction values are also more accurate in comparison with the accuracy achieved in a conventional X-ray examination apparatus. Corrected brightness values can be achieved which have a deviation of no more than approximately $\frac{1}{1000}$ from the correct brightness values. So-called frame flicker is thus substantially precluded. The accuracy is even so high that, if the circumstances in which X-ray images are picked up do not vary too much, a substantially disturbance-free composite image can be derived with a fixed set of correction values. Such a set of correction values is formed, for example by forming a suitable image on an exit screen of an X-ray image intensifier by irradiating a suitable test object, a so-called phantom, by means of the X-ray beam. The test object is preferably an object of uniform density wherefrom ideally an image of uniform brightness is formed. The X-ray image intensifier acts as an X-ray detector. It is alternatively possible to present a suitable optical image directly to the image pick-up apparatus. In the latter case the image pick-up apparatus is uncoupled from the X-ray detector for the picking up of the test images.

When an image pick-up apparatus is used to derive electronic sub-image signals from sub-images of the optical image and to compose an electronic image signal on the basis of these sub-image signals, a composite image of high diagnostic quality is formed. This is achieved because disturbances due to differences between the sub-image signals which do not relate to image information in the optical image are counteracted in the electronic image signal of the composite image. Because the dark image signal is also involved in the extraction of the gain correction values, accurate gain correction values are derived. As a result, the composite image can be reproduced in such a manner, for example on a monitor or as a hard copy, that small details of low contrast are still suitably reproduced. Notably inaccuracies caused by differences in the offsets of the sub-image signals are avoided. Differences between the offsets of individual image sensors are caused inter alia by differences in the dark current of these image sensors.

A further preferred embodiment of an X-ray examination apparatus according to the invention is characterized in that the correction unit includes an analog-to-digital converter for deriving digital gain correction values from differences between the relative gain values and the approximated gain value.

In order to derive the test image signals, the first gain value and the offset are preferably chosen so that the range of the relevant variations of the gain and/or offset correction values suitably corresponds to the dynamic range of the analog-to-digital converter. As a result, the capacity of the analog-to-digital converter is used as well as possible, the introduction of errors by the digitization of the gain correction values then being avoided. The accurately digitized gain correction values are used for deriving the corrected brightness values in digital form in the digital correction unit. Noise contributions to said corrected brightness values are thus counteracted. A further advantage of digitized correction values consists in that they can be readily stored and that they hardly introduce inaccuracies when used in arithmetical operations such as the calculation of the corrected brightness values.

The above embodiments of an image pick-up apparatus according to the invention are suitable, while maintaining all of said advantages, for use in an X-ray examination apparatus including an image pick-up apparatus in which an electronic image signal is derived from an optical image by means of a single image sensor, but also in an X-ray examination apparatus including an image pick-up apparatus in which electronic sub-image signals are derived from sub-images of the optical image by means of one or more individual image sensors, an electronic image signal for a composite image being derived from said electronic sub-image signals by a combination unit. Said composite image has a spatial resolution higher than that of the sub-images and hence has a higher diagnostic quality.

The above embodiments of an image pick-up apparatus according to the invention are suitable not only for picking up an optical image derived from an X-ray image, but also for picking up optical images from other sources. For example, an image pick-up apparatus of this kind can be used as a camera for forming an electronic image signal of a composite image of a scene.

It is a further object of the invention to provide methods for more accurate correction of electronic image signals and/or for maintaining compensation of undesirable differences between signal levels of individual sub-image signals with changing circumstances in which the sub-image signals are generated. This further object is achieved by means of the method according to the invention which is characterized in that a dark image signal is formed, that one or more test image signals are derived from the optical image, and that the correction values are derived from the dark image signal and said test image signals.

In a contemporary image pick-up apparatus the functions of the correction unit and the combination units can be performed by a suitably programmed computer or a special-purpose electronic (micro)processor.

These and other aspects of the invention will be apparent from and elucidated with reference to the embodiments described hereinafter.

DESCRIPTION OF THE PREFERRED EMBODIMENTS

Figure 1:
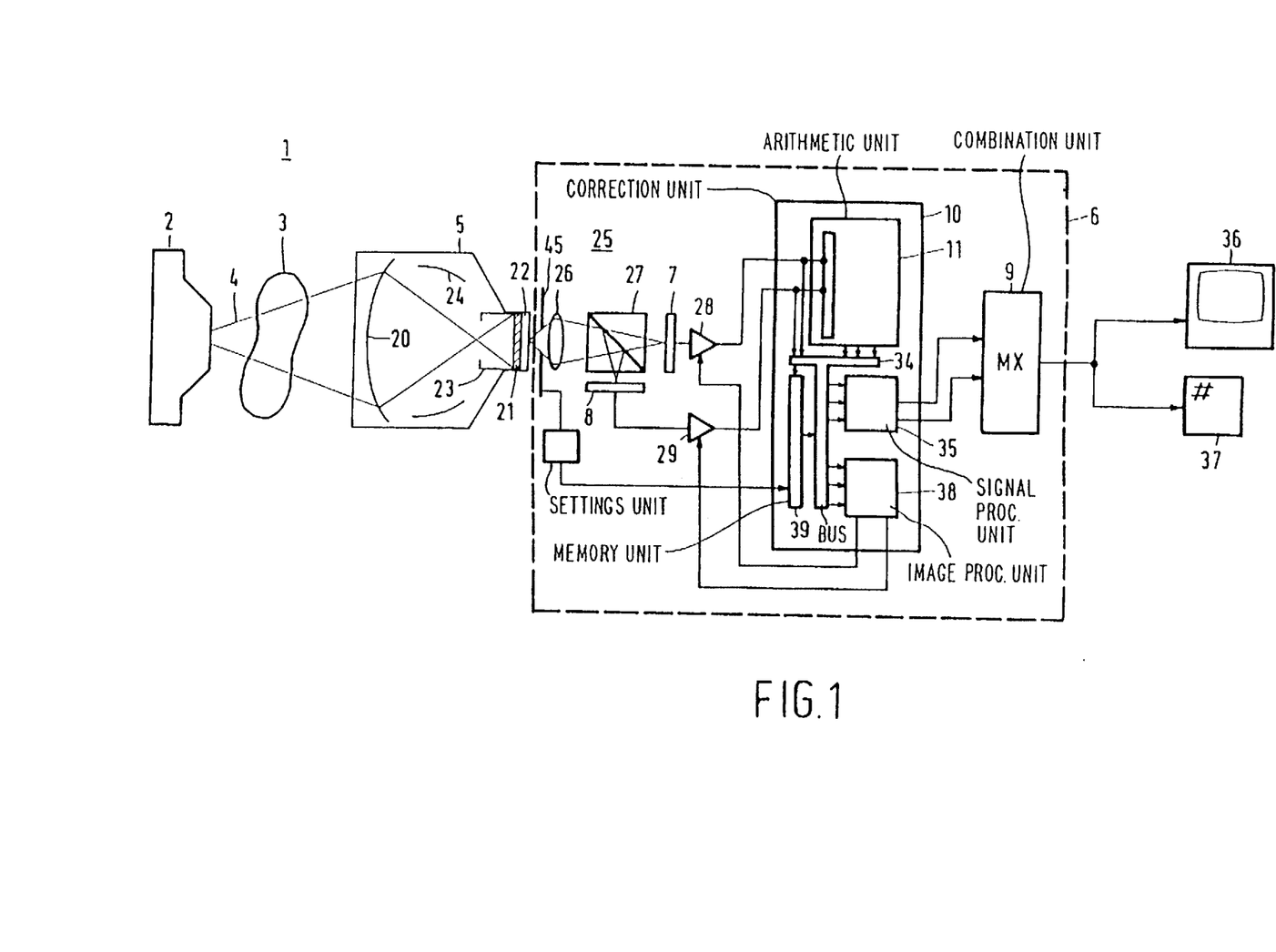
FIG. 1 shows diagrammatically an X-ray examination apparatus according to the invention, including an image pick-up apparatus with two image sensors.

FIG. 1 shows diagrammatically an X-ray examination apparatus according to the invention which includes an image pick-up apparatus 6 with two image sensors 7, 8.

The X-ray source 1 emits an X-ray beam for irradiating an object, for example a patient to be examined. Due to local differences in absorption of X-rays in the patient arranged between the X-ray source 1 and the X-ray detector 5, an X-ray image is formed on an X-ray sensitive surface of the X-ray detector 5. In the embodiment shown in FIG. 1 the X-ray detector 5 is formed by an X-ray image intensifier. The X-ray sensitive surface is formed by an entrance screen 20 which converts incident X-rays into an electron beam. The electron beam generates an optical image on a phosphor layer 21 on an exit window 22. For example, the phosphor layer emits visible light, ultraviolet radiation or infrared radiation. The electron beam is guided from the entrance screen to the exit window 22 by means of a hollow anode 23 and alignment electrodes 24. The hollow anode 23, the alignment electrodes 24 and the entrance screen form part of an electron-optical system which images the entrance screen electron-optically on the exit screen.

The exit window is imaged on the image sensors 7, 8 by means of an optical system 25 which includes a lens 26 and a splitting prism 27 in the present embodiment. Evidently, instead of the splitting prism 27 use can be made of a partly transparent mirror. It will also be evident that the optical system can be arranged so that a part of the exit window is imaged. The optical systems splits the light from the exit window 22 into two sub-beams which are focused on the individual image sensors 7 and 8. The image sensors 7, 8 are, for example CCD sensors which include a large number of photosensitive elements and are positioned relative to the splitting prism 27 in such a manner that image elements of the optical image which are imaged on photosensitive elements of one image sensor are imaged in intermediate spaces between photosensitive elements of the other image sensor. For example, the individual image sensors pick up alternating bands of the optical image.

Each of the image sensors supplies an electronic sub-image signal which contains signal levels representing brightness values in the sub-images. The electronic sub-image signals are combined in the combination unit 9 so as to form an electronic image signal whose signal levels represent brightness values for the composite image. In the direction transversely of the image lines, the composite image has a spatial resolution which has approximately been doubled in comparison with the sub-images picked up by the individual sensors. The image sensors 7, 8 may alternatively be arranged in such a manner that one half of the optical image, for example the lower half and the upper half, is imaged on each of the individual image sensors. Preferably, there is a common, overlapping part of the optical image which is picked up by both image sensors. Each of the individual image sensors supplies a sub-image signal which represents approximately half the optical image. Via the combination unit, the sub-image signals are combined so as to form an electronic image signal containing image information of the complete optical image. Each of the image sensors is coupled to a variable amplifier 28, 29 whereby the electronic sub-image signals can be amplified as desired.

The electronic sub-image signals are applied to the correction unit 10 which derives corrected sub-image signals from the electronic sub-image signals and correction values. The corrected sub-image signals represent corrected brightness values. The correction unit 10 includes an arithmetic unit 11 for calculating the correction values from test image signals and dark image signals. The correction unit also includes a signal processing unit 35 for deriving the corrected brightness values from the correction values and the signal levels of the electronic sub-image signals. The arithmetic unit 11 and the image sensors are coupled to the signal processing unit 35 via a bus 34. The correction values calculated by the arithmetic unit 11 and the electronic sub-image signals are applied to the signal processing unit 35 via the bus 34. Details of the arithmetic unit 11 will be described hereinafter with reference to FIG. 3. The corrected brightness values are applied to the combination unit 9 as corrected electronic sub-image signals. The electronic image signal formed from the corrected sub-image signals by the combination unit 9 is applied to a monitor 36 or to a processing unit 37. The image information of the X-ray image can be displayed on the monitor 36; the processing unit 37 can perform further image processing operations on the electronic image signal of the composite image. The correction unit 10 also includes a control unit 38 which applies control signals to respective control inputs of the amplifiers 28 and 29 on the basis of the correction values. The control unit 38 receives the correction values from the arithmetic unit via the bus 34. For example, the control signals adjust the amplifiers 28, 29 in such a manner that differences between the signal levels of the electronic sub-image signals are comparatively small. At this setting of the amplifiers only small corrections are required to form an image signal of the composite image. Because such corrections are small, they can be performed with a high accuracy.

The correction values can also be stored in a memory unit 39. If the circumstances in which successive images are picked up do not change excessively, it is not necessary to calculate the correction values each time anew by means of the arithmetic unit 11; instead the correction values can then be derived from the memory unit 39 by the signal processing unit 38. If desirable, different sets of correction values can be stored in the memory unit, each set corresponding to individual settings of the X-ray examination apparatus provided to memory unit 39 by settings unit 52. For example, separate sets of correction values can be stored for separate settings of a diaphragm 45 whereby the amount of light reaching the image sensors is adjusted.

Figure 2:
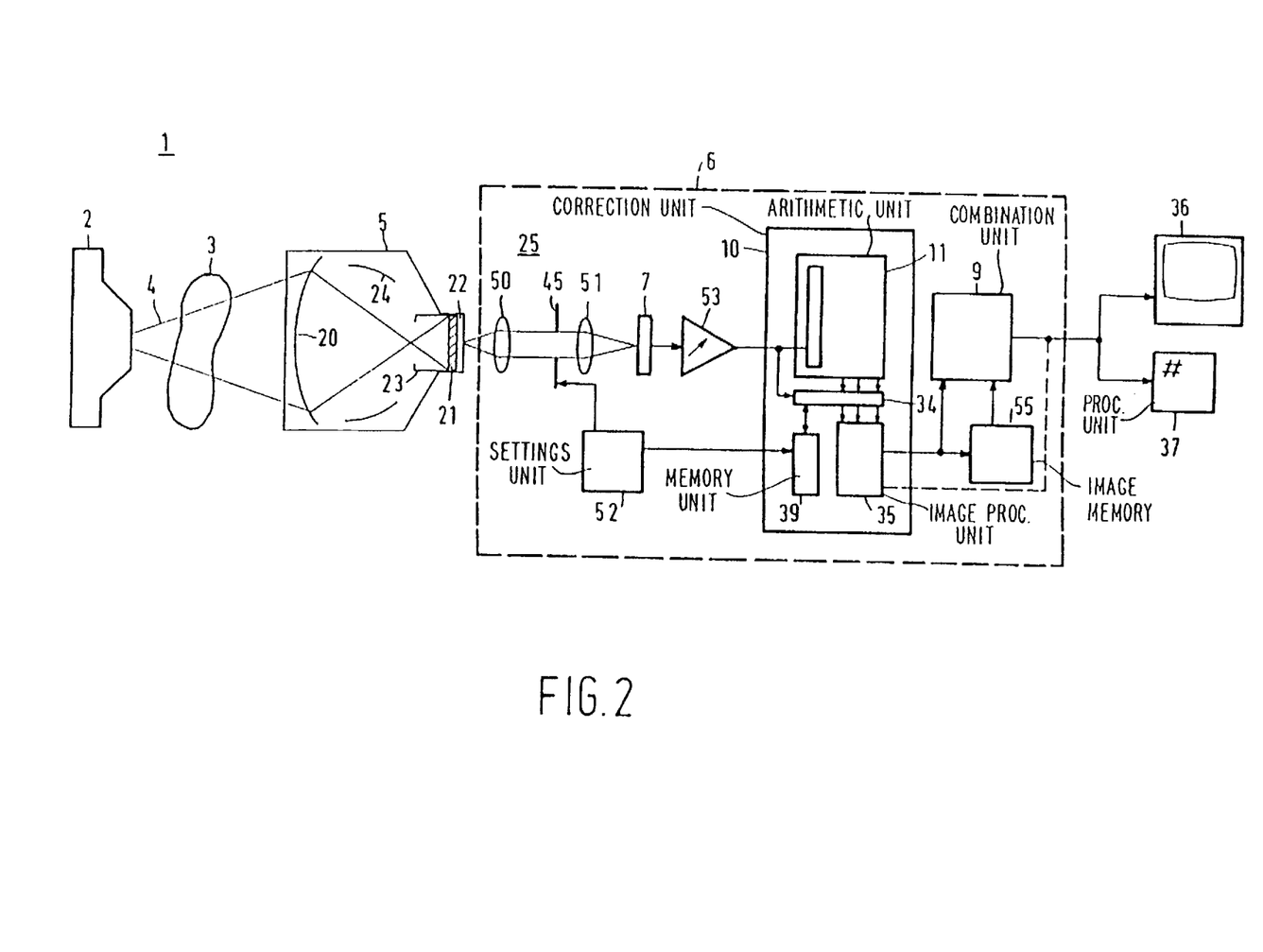
FIG. 2 shows diagrammatically an X-ray examination apparatus according to the invention which includes a single image sensor.

FIG. 2 shows diagrammatically an X-ray examination apparatus according to the invention which includes a single image sensor. The image pick-up apparatus 6 of this embodiment includes a single image sensor 7. The optical image on the exit window 22 is imaged on the image sensor 7 by means of an optical system 25 which includes two lenses 50, 51. One lens forms a parallel beam from the light emanating from the exit window, and the other lens 51 focuses said parallel beam onto the image sensor 7. From the image on the exit window 22 the image sensor derives an electronic image signal which has been amplified to a desired degree by means of a variable amplifier 53. The electronic image signal is applied to the correction unit 10. The signal levels of the electronic image signal represent brightness values of the optical image on the exit window. For various reasons the variation of said brightness values contains a component which varies comparatively slowly relative to the variations representing image information. Part of the light emanating from the exit window is not conducted to the image sensor 7 by the optical system 25. Notably a part of the light from the outer part of the exit window bypasses the lens 50 and a part of the light of the parallel beam is intercepted by a diaphragm 45 between the lenses 50 and 51. In the light beam reaching the image sensor 7, therefore, a brightness variation occurs which consists in that the brightness values, or the signal levels, decrease from the center of the image towards its edge. This variation does not represent image information in the optical image and is referred to as vignetting. The electronic image signal is applied to the correction unit 10 which derives correction values from the electronic image signal and outputs a corrected electronic image signal which represents corrected brightness values. The correction values are derived from the electronic image signal by means of the arithmetic unit 11. The arithmetic unit 11 and the output of the amplifier 53 are coupled to the signal processing unit 35 via the bus 34. The correction values and the electronic image signal are applied to the signal processing unit 35 which applies a corrected electronic image signal to the monitor 36 and/or the image processing unit 37. The corrected electronic image signal is applied to the monitor 36 and/or the image processing unit 37 as denoted by the dashed line in FIG. 2. It is alternatively possible to apply a corrected electronic image signal to an image memory 55. The stored corrected electronic image signal and a corrected electronic image signal of a next image can be used as corrected electronic sub-image signals wherefrom the combination unit 9 forms an electronic image signal of a composite image.

Figure 3:
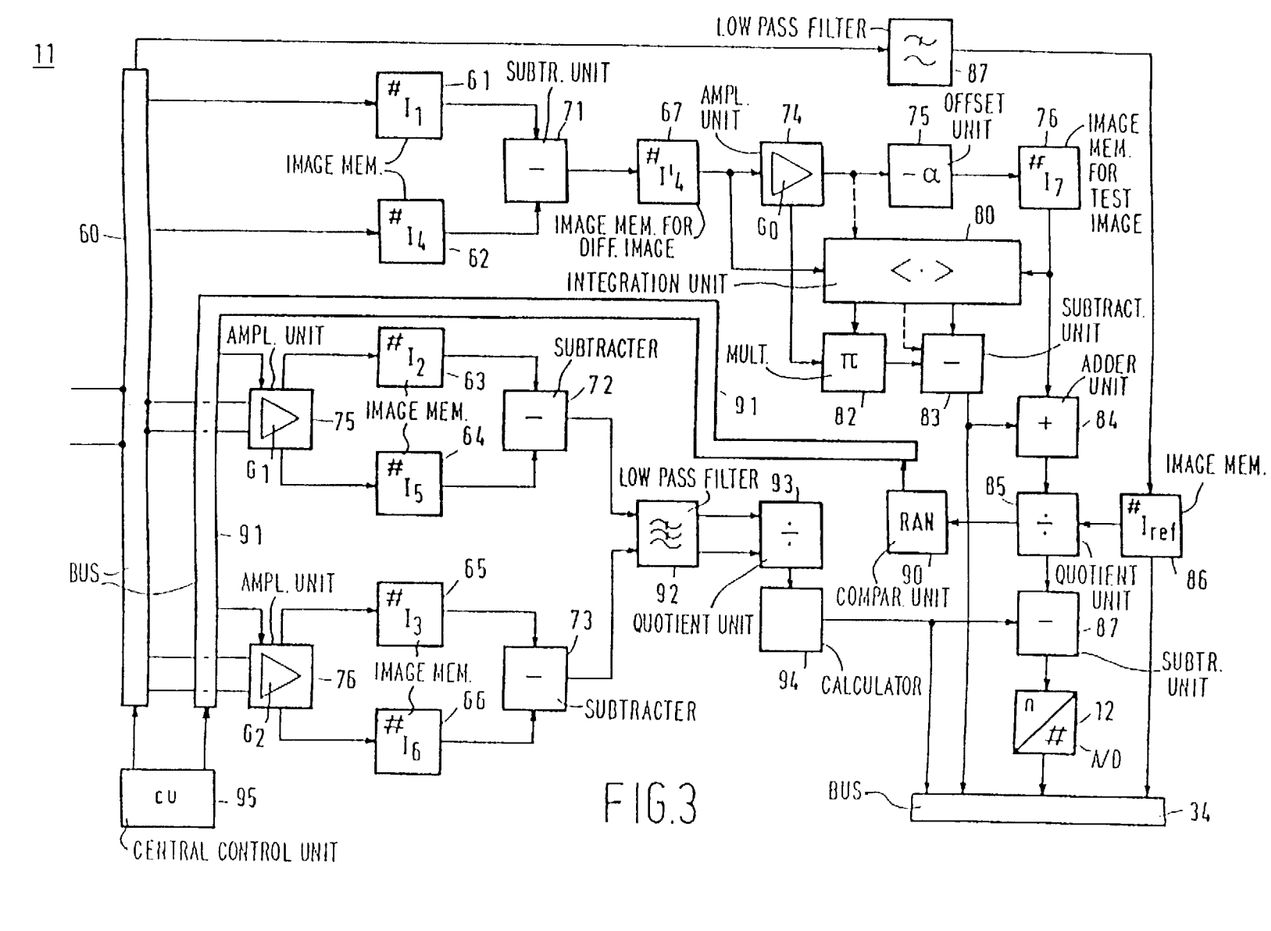
FIG. 3 shows diagrammatically a correction unit of an X-ray examination apparatus according to the invention.

FIG. 3 shows diagrammatically a correction unit of an X-ray examination apparatus according to the invention.

The electronic sub-image signals of the amplifiers 28, 29 are supplied via a bus 60. The dark image signal is also transported via this bus. The dark image signal is obtained by applying output signals of the amplifiers 28, 29 to the correction unit 10 when the X-ray source does not deliver X-rays and hence no optical image is formed on the exit window. An electronic dark image signal is applied to an image memory 61 and stored as a dark image $I_1$. An electronic sub-image signal is applied to the image memory 62 and stored as an image $I_4$. The stored image $I_4$ is the sub-image picked up by one of the image sensors 7, 8. The dark image signal and the electronic sub-image signal preferably originate from the same image sensor. Furthermore, the dark image signal and the electronic sub-image signal preferably relate to images of substantially the same dimensions. The images $I_1$ and $I_4$ have preferably been picked up with the same settings of the amplifiers 28, 29. This offers the advantage that the dark current contribution in the images $I_1$ and $I_4$ is substantially the same. A difference image $I_4'$ is formed by a subtraction unit 71 and stored in an image memory 67. The difference image $I_4'$ is substantially independent of the dark current contribution to the electronic sub-image signal. An amplifier unit 74 amplifies the image $I_4'$ pixel by pixel with a gain ratio $G_0$ and an offset value $\alpha$ is subtracted from the amplified brightness values by means of an offset unit. Evidently, it is also possible to subtract an offset value $\alpha$ from the brightness values of the image $I_4'$ first, the difference values then being amplified. The cooperating amplifier unit 74 and the offset unit 75 form a test image signal $I_7$ which is stored as a test image $I_7$ in an image memory 76. The following relation exists between the test image $I_7$, the difference image $I_4'$, the image $I_4$ and the dark image $I_1$:

$$I_7 = G_0 I_4' - \alpha,$$

where $$I_4' = I_4 - I_1.$$

The amplifier unit 74 and the offset unit 75 are adjusted so that the range of the brightness variations in the test image $I_7$ corresponds as well as possible to brightness variations in the image picked up by the image sensor 7 or 8. The test image $I_7$ is applied to an integration unit 80. Furthermore, the output of the amplifier unit 74 is coupled to the integration unit 80 as denoted by a dashed connection in FIG. 3. The difference image $I_4'$, amplified with the gain ratio $G_0$, is applied to the integration unit. The integration unit 80 derives averaged signals $<I_7>$ and $<G_0 I_4'>$ from $I_7$. The averaged signals are subtracted in a subtraction unit 83 and the result constitutes the offset value subtracted from the amplified difference signal $(G_0 I_4')$ by the offset unit 75. A dashed connection between the integration unit 80 and the subtraction unit 83 indicates that the averaged signal $<G_0 I_4'>$ is applied to the subtraction unit. It is alternatively possible to derive an averaged signal $<I_4'>$ from the difference image $I_4'$ by means of the integration unit 80. To this end, the output of the image memory 67 is connected to the integration unit 80. The averaged difference image $<I_4'>$ is multiplied, using a multiplier 82, by the gain factor $G_0$ used by the amplifier unit 74. This gain factor can be derived from the images $I_7$ and $I_4$, for example from statistical variations in the images $I_4$ and $I_7$, such as the ratios of the variances of the maximum values of the brightness values of the images $I_7$ and $I_4$, respectively. A signal level $G_0<I_4'>$ then appears on the output of the multiplier. The integration unit 80 and the multiplier 82 are coupled to the subtracter 83 by way of their respective outputs. The subtracter 83 calculates the difference $<G_0, I_4'> - <I_7> = \alpha$, which amounts to exactly the offset value used by the offset unit 75. The offset value $\alpha$ is added to the test image $I_7$ by an adder unit 84; to this end, outputs of the image memory 76 and the subtracter 83 are coupled to the adder unit 84. The output of the adder unit thus supplies a signal level $I_7 + \alpha$ which represents the brightness values of the test image $I_7$ whereto the offset value a used by the offset unit 75 has been added. In order to determine the gain correction values, the ratio $\gamma$ of the signal level $I_7 + \alpha$ to a reference image $I_{ref}$ is determined pixel by pixel by means of a quotient unit 85. The reference values are stored in an image memory 86 as a reference image $I_{ref}$. When use is made of an image pick-up apparatus including two images sensors 7, 8, preferably the test image $I_7$ is derived from the image signal of one image sensor and the reference image is derived from the other image sensor. A low-pass filter 87, being coupled to the relevant image sensor via the bus 60, derives a low frequency component of the electronic sub-image signal of the relevant image sensor. This low frequency component is stored in the image memory 86 as a reference image. A comparison unit 90 derives the value range from the ratios $\gamma$ for each of the pixels, or for groups of pixels, which value range is the (smallest) interval in which the values of the ratios $\gamma$ are situated. From the ratios $\gamma$ a common term $\beta$ is subtracted in subtraction unit 96, which term $\beta$ is chosen so that the range of the difference $\gamma - \beta$ corresponds as well as possible to the range of the analog-to-digital converter 12. The analog-to-digital converter derives accurate digital values $\gamma\#$ from the differences $\gamma - \beta$, which digital values are applied to the bus 34. Because, generally speaking, the value of $\beta$ is substantially larger than the differences $\gamma - \beta$, the common term indicating a comparatively good estimate of the ratio of the signal levels $I_7 + \alpha$ and of the brightness values of the reference image, is also referred to as an approximated gain value in this Application. In the present Application the differences $\gamma - \beta$ are also referred to as relative gain values. These relative gain values correct the approximated gain value $\beta$.

For accurate determination of the common term A, further test images $I_5$ and $I_6$ are derived. The test image $I_5$ is derived from an electronic sub-image signal from one of the image sensors by amplifying said electronic sub-image signal by a gain factor $G_1$ in an amplifier unit 75. An amplifier unit 76 derives the test image $I_6$ by amplifying the electronic sub-image signal by a gain factor $G_2$. Instead of providing the arithmetic unit 11 with its own amplifier units 75, 76 it is also possible, of course, to use the amplifiers 27, 28 for deriving the test images $I_5$ and $I_6$ from the electronic sub-image signal. The respective amplifier units or the amplifiers 27, 28 derive dark images $I_2$ and $I_3$ from the electronic dark image signal by amplifying the electronic dark image signal by respective gain factors $G_1$ and $G_2$. The dark images $I_2$, $I_3$ and the test images $I_5$, $I_6$ are stored in respective image memories 63, 64, 65 and 66. It will be evident that the individual image memories shown in FIG. 3 can also be combined so as to form a common image memory of sufficient capacity to store the individual test, reference and dark images. The gain factors $G_1$ and $G_2$ are suitably chosen on the basis of the value range of the ratios y. To this end, control inputs of the amplifier units 75, 76 are coupled to the comparison unit 90 via a bus 91. When the amplifiers 28, 29 are used instead of the own amplifier units 75, 76 of the arithmetic unit 11, the comparison unit is coupled to the control inputs of the amplifiers 28, 29. Preferably, the gain factors $G_1$ and $G_2$ are chosen on the basis of the smallest and the largest value of the ratio $\beta$. A subtracter 72 forms a difference image $I_5' = I_5 - I_2$ and a subtracter 73 forms a difference image $I_6' =_6 - I_3$. The dark images $I_2$ and $I_3$ are amplified by the same gain factors as the test images $I_5$ and $I_6$, respectively. As a result, the dark images $I_2$ and $I_3$ constitute substantially the dark current contribution of the test images $I_5$ and $I_6$, respectively. Thus, the difference images $I_5'$ and $I_6'$ are rendered substantially independent of the dark current contribution. A low-pass filter 92 derives the DC components $<I_5'>$ and $<I_6'>$ from difference images $I_5'$ and $I_6'$. Instead of the low-pass filter, the integration unit 80 can also be used for deriving the DC components $<I_5'>$ and $<I_6'>$ from the difference images. To this end, the subtracters 72 and 73 should be coupled to the integration unit 80, for example via the bus 91. The ratio $<I_6'>/<I_5'>$ is derived by means of a quotient unit 93. This ratio is applied to a calculator 94 which derives the common term $\beta$ from said ratio. When a 10-bit analog-to-digital converter is used, 1,024 digital values are available for distribution of the values of $_i\#$. The common term $\beta$ then amounts to:

$$\beta = 1023/[(<I_6'>/<I_5'>)-1]$$

The values of $\beta$, $\#$, $\alpha$ and the brightness values of the reference image are applied to the signal processing unit 35 via the bus 34. Preferably, such values are used as signals having respective signal levels which represent the relevant values. The arithmetic unit 11 also includes a central control unit 95 which controls the signal traffic on the buses 60, 91 and to the bus 34.

The correction unit as shown in FIG. 3 is also suitable per se for providing particularly accurate correction values. Notably correction values can be provided for correction with a high resolution, for example images comprising 1k×1k or even 2k×2k pixels. To this end, an image is picked up of an object which is as homogeneous as possible, which image also comprises such a large number of pixels. If no disturbances were to occur, such an object would yield an image of substantially uniform brightness and hence an electronic image signal having a substantially constant signal level. This electronic image signal is applied to the image memory 62 as a test image $I_4$. The correction unit then applies particularly accurate correction values to the bus 34 for storage in a memory such as the memory unit 39. A suitable reference image is an image of uniform brightness, its brightness value being the mean brightness of a part (preferably the central part) of the optical image on the exit window. This uniform reference image can be used notably in the case of an image pick-up apparatus including a single image sensor. Preferably a maximum value of the signal level of the electronic image signal is then used as the reference value in the memory 86.

I claim:

1. An X-ray examination apparatus, comprising an X-ray detector for deriving an optical image from an X-ray image, an image pick-up apparatus for deriving an image signal from the optical image, and a correction unit for correcting the image signal by means of correction values, characterized in that the image pick-up apparatus is arranged to form a dark image signal, and that the correction unit is arranged to derive one or more test image signals from the optical image, and to derive the correction values from said test image signals and the dark image signal.

2. An X-ray examination apparatus as claimed in claim 1, characterized in that the correction unit is arranged to derive an offset correction value from one or more of the test image signals and the dark image signal, which offset correction value represents a difference between the minimum signal level of the electronic image signal and a zero level.

3. An X-ray examination apparatus as claimed in claim 1 characterized in that the correction unit is arranged to derive a gain correction value from the test image signals and the dark image signal, which gain correction value represents a ratio of a signal level of the electronic image signal to a reference value.

4. An X-ray examination apparatus as claimed in claim 1, characterized in that the correction unit is arranged to form a first test image signal, having a signal level which corresponds to a brightness value of the optical image, a second test image signal, having a signal level which corresponds to the sum of an offset and a brightness value of the optical image which has been amplified by a first gain value, and a first difference signal which corresponds to the difference between signal levels of the first test image signal and the dark image signal, and that the correction unit includes an arithmetic unit which is arranged to derive the first gain value from signal levels of the second test image signal and of the first difference signal, and the offset correction value from the first gain value and the signal levels of the second test image signal and of the first difference signal.

5. An X-ray examination apparatus as claimed in claim 4, characterized in that the arithmetic unit is arranged to derive the first gain value from statistical variations of the signal levels of the second test image signal and of the first difference signal, and the offset correction value $\alpha$ from the first gain value and mean values of the signal levels of the first difference signal and the second test image signal.

6. An X-ray examination apparatus as claimed in claim 1, characterized in that the correction unit is arranged to derive an offset-corrected electronic image signal from the electronic image signal and the offset correction value, to derive relative gain values for individual image elements in the optical image from signal levels of the offset-corrected electronic image signal and a reference value, to form a third and a fourth test image signal, having signal levels corresponding to brightness values of the optical image amplified by a second and a third gain value, respectively, and to form second and third difference signals which correspond to the difference between signal levels of second and third test image signals and the dark image signal, respectively, and that the arithmetic unit is arranged to derive an approximated gain value from signal levels of the second and third difference signals, which approximated gain value represents an estimate for the relative gain values.

7. An X-ray examination apparatus as claimed in claim 6, characterized in that the correction unit includes an analog-to-digital converter for deriving digital gain correction values from differences between the relative gain values and the approximated gain value.

8. An X-ray examination apparatus as claimed in claim 2, characterized in that the correction unit is arranged to derive a gain correction value from the test image signals and the dark image signal, which gain correction value represents a ratio of a signal level of the electronic image signal to a reference value.

9. An X-ray examination apparatus as claimed in claim 2, characterized in that the correction unit is arranged to form a first test image signal, having a signal level which corresponds to a brightness value of the optical image, a second test image signal, having a signal level which corresponds to the sum of an offset and a brightness value of the optical image which has been amplified by a first gain value, and a first difference signal which corresponds to the difference between signal levels of the first test image signal and the dark image signal, and that the correction unit includes an arithmetic unit which is arranged to derive the first gain value from signal levels of the second test image signal and of the first difference signal, and the offset correction value from the first gain value and the signal levels of the second test image signal and of the first difference signal.

10. An X-ray examination apparatus as claimed in claim 3, characterized in that the arithmetic unit is arranged to derive the first gain value from statistical variations of the signal levels of the second test image signal and of the first difference signal, and the offset correction value a from the first gain value and mean values of the signal levels of the first difference signal and the second test image signal.

11. An X-ray examination apparatus as claimed in claim 3, characterized in that the arithmetic unit is arranged to derive the first gain value from statistical variations of the signal levels of the second test image signal and of the first difference signal, and the offset correction value a from the first gain value and mean values of the signal levels of the first difference signal and the second test image signal.

12. An X-ray examination apparatus, comprising an X-ray source for emitting an X-ray beam in order to form an X-ray image of an object, an X-ray detector for deriving an optical image from the X-ray image, an image pick-up apparatus which includes one or more image sensors for deriving electronic sub-image signals from sub-images of an optical image, a combination unit for forming, on the basis of the electronic sub-image signals, an electronic image signal for a composite image, and a correction unit for deriving corrected brightness values of the sub-images from correction values and the electronic sub-image signals, characterized in that the correction unit is arranged to form a dark image signal, to derive one or more test image signals from the optical image, and to derive the correction values from said test image signals and the dark image signal.

13. A method of correcting an electronic image signal, in which the electronic image signal is derived from an optical image by means of an image sensor, and corrected brightness values are derived from the electronic image signal and correction values, characterized in that a dark image signal is formed, one or more test image signals are derived from the optical image, and the correction values are derived from the dark image signal and said test image signals.

14. A method of correcting an electronic image signal, in which electronic sub-image signals are derived from sub-images of the optical image by means of one or more image sensors, corrected brightness values are derived from the electronic sub-image signals and correction values, characterized in that a dark image signal is formed, one or more test image signals are derived from the optical image, and the correction values are derived from the dark image signal and said test image signals.

\* \* \* \* \*